United States Patent [19]
Varn

[11] Patent Number: 5,362,304
[45] Date of Patent: Nov. 8, 1994

[54] THORACIC LUMBAR SACRAL ORTHOSIS DEVICE

[75] Inventor: Harold T. Varn, Lawrenceville, Ga.

[73] Assignee: Restorative Care of America Incorporated, Clearwater, Fla.

[21] Appl. No.: 967,505

[22] Filed: Oct. 28, 1992

[51] Int. Cl.$^5$ .............................................. A61F 5/02
[52] U.S. Cl. ........................................ 602/19; 2/44; 2/92
[58] Field of Search ................ 602/19, 6, 7; 2/44, 2/45, 92; 126/669, 674; 441/106, 108, 111, 115, 132

[56] References Cited

U.S. PATENT DOCUMENTS

| | | | |
|---|---|---|---|
| 3,331,367 | 7/1967 | Hastings | 602/19 |
| 3,771,513 | 11/1973 | Velazquez | 602/19 |
| 4,655,716 | 4/1967 | Lucius | 441/106 |
| 4,820,221 | 4/1989 | Aubrey | 441/106 |
| 4,986,805 | 6/1990 | Piati, Jr. | 441/106 |
| 5,007,412 | 4/1991 | DeWall | 2/44 X |
| 5,060,313 | 10/1991 | Neuhalfen | 2/45 X |
| 5,074,292 | 12/1991 | Cox | 602/7 |
| 5,157,792 | 10/1992 | Allen et al. | 2/92 X |

Primary Examiner—Richard J. Apley
Assistant Examiner—Beverly A. Meindl
Attorney, Agent, or Firm—Zarley, McKee, Thomte, Voorhees & Sease

[57] ABSTRACT

A thoracic lumbar sacral orthosis device includes a jacket having opposite side portions, a back portion, and a releasable front portion. The back portion is integrally formed with the side portions. A compartment is formed within the jacket for receiving padding and a brace member, with the padding being positioned between the patient and the brace member. The brace member is formed from a moldable material so as to conform to the patient's spine. The side portions of the jacket include pockets for receiving side supports to provide lateral trunk stability for the patient. Auxiliary pads can be attached to the side portions to provide additional lateral stability when the patient is sitting in a chair.

15 Claims, 3 Drawing Sheets

THORACIC LUMBAR SACRAL ORTHOSIS DEVICE

BACKGROUND OF THE INVENTION

Back braces of numerous types have been used in the past for supporting the upper and lower back and to provide corrective therapy for the spine. One commonly used form of brace, known as a Knight Taylor, is a metal brace comprising a thoracic band, a pelvic band, and paraspinal bars extending between the bands. The Knight Taylor brace had little, if any, padding between the rigid metal bars and the patient. Thus, patients often complained about pressure caused by the hard braces. Some Knight Taylor devices were provided with an apron front or a corset front. Besides being uncomfortable, the Knight Taylor devices did not provide lateral trunk stability and did not prevent forward slumping of the patient.

Therefore, a primary objective of the present invention is the provision of an improved thoracic lumbar sacral orthosis device.

A further objective of the present invention is the provision of a back brace jacket having padding between the rigid or semi-rigid brace members and the patient.

Another objective of the present invention is provision of a device for providing corrective support to the upper and lower spine.

A further objective of the present invention is the provision of a back brace which maintains the natural S-shaped curve in the spine.

A further objective of the present invention is the provision of a back brace which provides lateral trunk stability for the patient.

Another objective of the present invention is the provision of a back brace which prevents forward slumping of the patient.

A further objective of the present invention is the provision of a back brace wherein the brace members are made from a thermoplastic material which can be molded to accommodate a particular patient's spine.

Still another objective of the present invention is the provision of a back brace device having auxiliary side pads for lateral support when the patient is sitting in a chair.

Still another objective of the present invention is the provision of an improved back brace which is economical to manufacture, and durable and effective in use.

These and other objectives will become apparent from the following description of the invention.

SUMMARY OF THE INVENTION

The thoracic lumbar sacral orthosis device of the present invention is in the form of a jacket having padding and brace members therein. More particularly, the jacket is substantially U-shaped, having opposite side portions and an interconnecting back portion. A compartment is formed within the jacket for enclosing the brace member and padding.

The brace member is formed from a thermoplastic material, such as Kydex, which is moldable, flexible, and has a high memory characteristic. Thus, the brace can be heated and formed to each particular patient's spine. The brace member includes a thoracic band, a pelvic band, and paraspinal bars extending between the bands. Each band has opposite ends which are received within pockets on the padding, such that the padding is positioned between the brace member and the patient. An access opening in the lower end of the jacket allows the brace member and padding to be positioned within or removed from the jacket. Each side portion of the jacket also includes a pocket having a rigid or semi-rigid support therein for providing lateral trunk stability. A front apron is provided on the jacket so as to define a three point pressure system, including the front apron, the pelvic band, and the thoracic band. This three point pressure system allows for corrective support of the upper and lower spine so as to help maintain the spine in a natural S-shaped curve. The front apron also has a pocket therein with a removable rigid or semi-rigid support plate.

The jacket includes a pair of adjustable axilla straps which extend over the shoulders and under the arms so as to prevent the patient from slumping forwardly. A pair of removable side pads can be fastened to each side of the jacket for providing lateral trunk support to the patient sitting in a chair, without securing the pads to the chair.

DESCRIPTION OF THE PREFERRED EMBODIMENT

Figure 1:
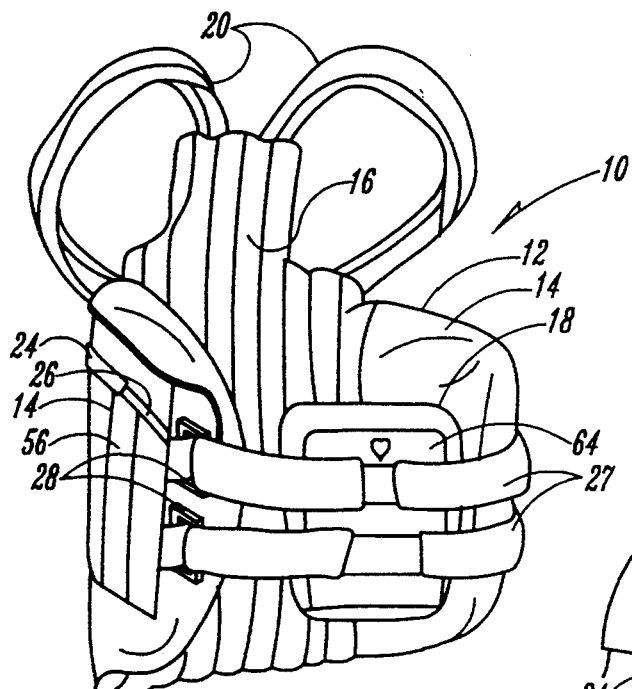
FIG. 1 is a perspective view of the thoracic lumbar sacral orthosis device of the present invention.
Figure 2:
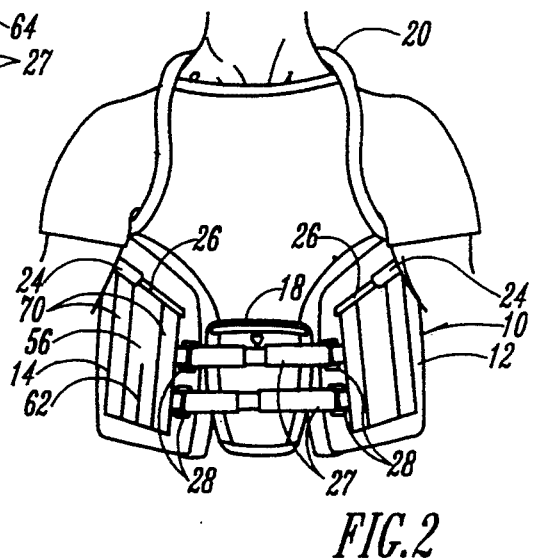
FIG. 2 is a front view of the device as worn by a patient.
Figure 3:
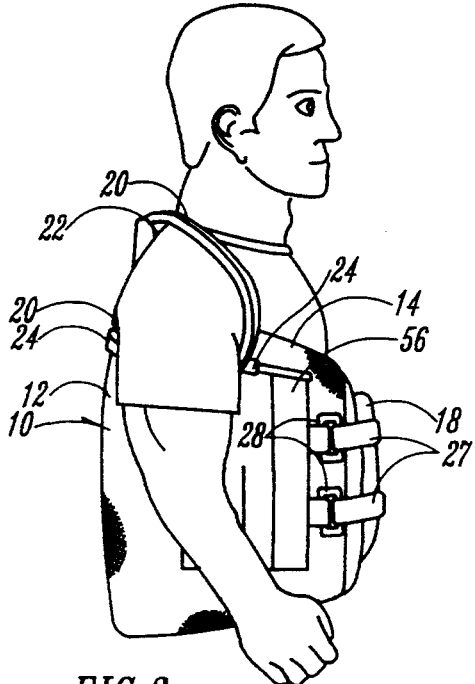
FIG. 3 is a side view of the device as worn by a patient.
Figure 4:
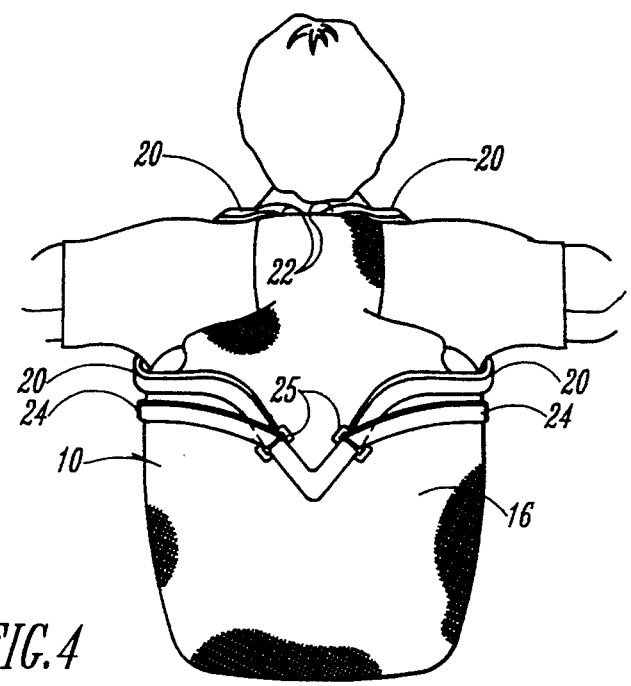
FIG. 4 is a rear view of the device as worn by a patient.
Figure 5:
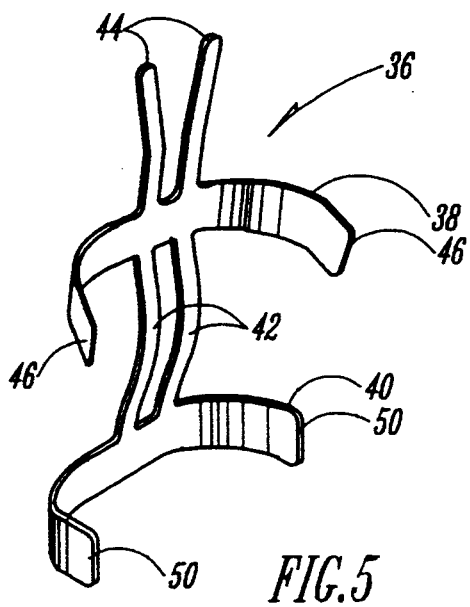
FIG. 5 is a perspective view of the brace member.
Figure 6:
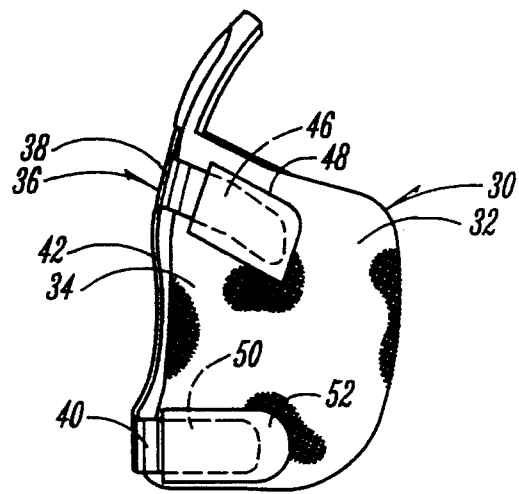
FIG. 6 is a side elevation view of the padding with the brace member mounted thereon.
Figure 7:
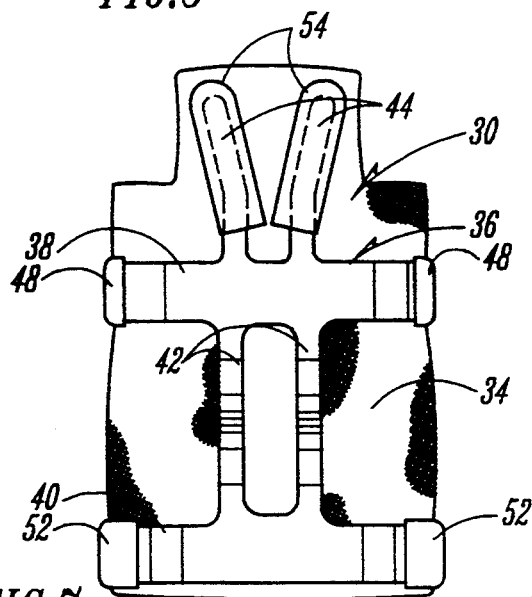
FIG. 7 is a rear elevation view of the brace member mounted on the padding.

In the drawings, the thoracic lumbar sacral orthosis device of the present invention is generally designated by the reference numeral 10. The device 10 includes a jacket 12 having opposite side portions 14, a back portion 16 interconnecting the opposite side portions 14, and a front apron 18. A pair of axilla straps 20 each have a first end 22 secured to the back portion 16 adjacent the top thereof. An opposite end 24 on each strap 20 extends through a loop 25 secured to the back portion 16 of the jacket, and then to a securement means, such as VELCRO strip 26. Straps 20 are thus adjustable. The front apron 18 is adjustably secured to the opposite side portions 14 by a pair of VELCRO straps 27 which are sewn to the apron 18 and which have opposite ends extending through loops 28.

The jacket 12 has an internal U-shaped compartment conforming substantially to the shape of the side portions 14 and the back portion 16. A U-shaped padding member 30 having opposite side portions 32 and an interconnecting back portion 34 is adapted to fit within the compartment.

A flexible brace member 36 is removably secured to padding member 30. Brace member 36 includes a horizontally disposed thoracic band 38, a horizontally disposed pelvic band 40, and a pair of paraspinal bars 42 extending between the bands 38 and 40. Extensions 44 from the paraspinal bars 42 extend upwardly beyond the thoracic band 38. The thoracic band 38 and the pelvic band 40 are each U-shaped. The thoracic band includes terminal ends 46 which are adapted to be received within pockets 48 on the padding member 30. The pelvic band 40 includes opposite terminal ends 50 which are adapted to be received within pockets 52 on the padding member 30. The upper extensions 44 of the paraspinal bars 42 are adapted to be received within pockets 54 on the padding member 30. The jacket 12 has an access opening (not shown) along the bottom edge to allow the padding member 30 and the brace member 36 to be removed from the compartment. The opening can be closed by any convenient means, such as VELCRO.

The brace member 36 is made of a thermoplastic material, such as Kydex, which can be molded so as to conform to each particular patient's spine. The material is flexible, and has a high memory characteristic so that once the material is heated and formed to the patient's spine, it will maintain the desired configuration. The brace member will therefore provide corrective support to the spine and maintain the spine in its natural S-shaped curvature. The padding member 30 resides between brace member 36 and the patient so as to eliminate pressure points and provide comfort for the patient.

Figure 8:
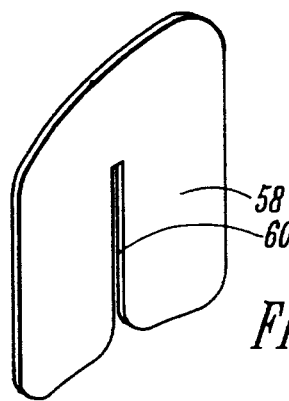
FIG. 8 is a perspective view of the side support plate.
Figure 9:
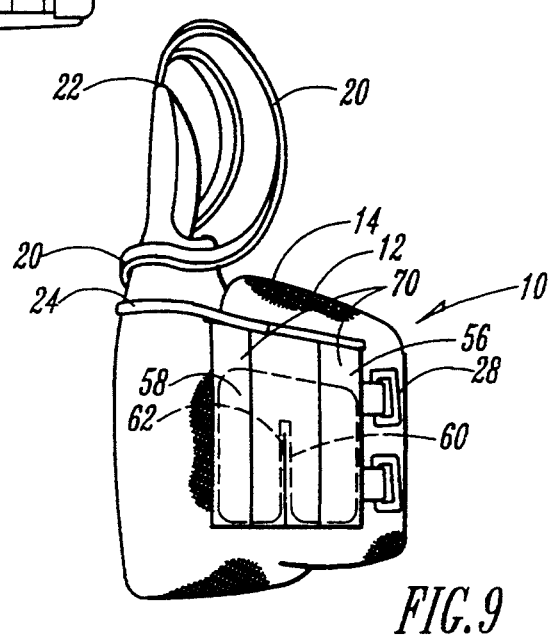
FIG. 9 is a side elevation view of the device showing the side support plate within a side pocket on the jacket.
Figure 10:
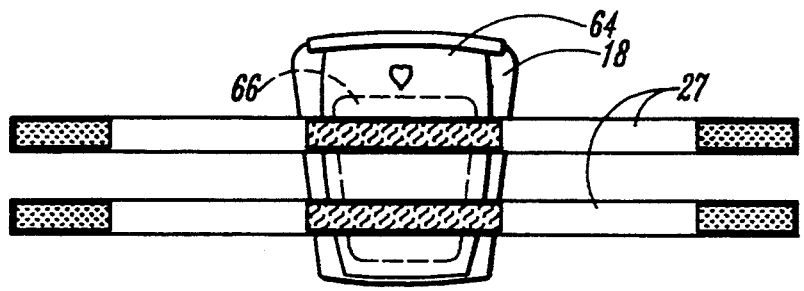
FIG. 10 is a front elevation view showing the front apron with a front support plate therein.
Figure 11:
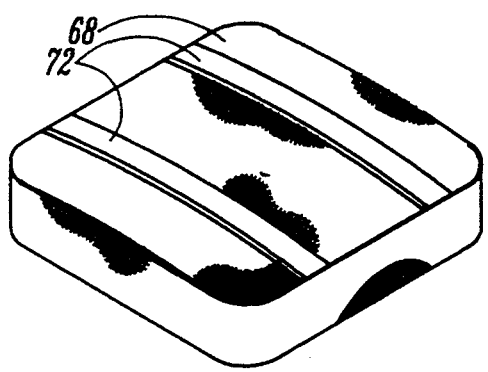
FIG. 11 is a perspective view of an auxiliary side pad for use on the device.
Figure 12:
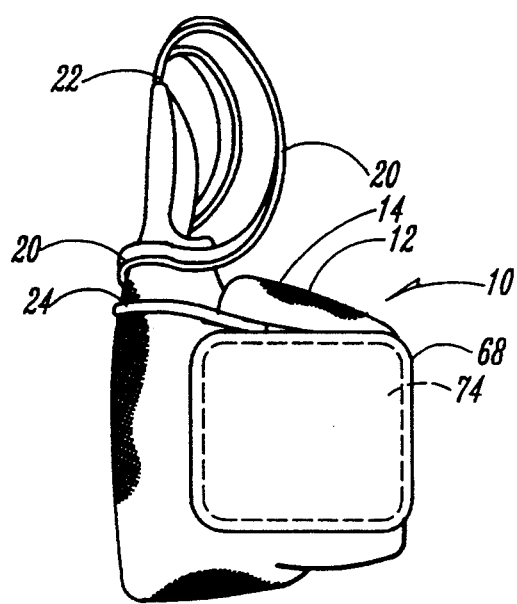
FIG. 12 is a side elevation view showing the auxiliary pad secured to the device.
Figure 13:
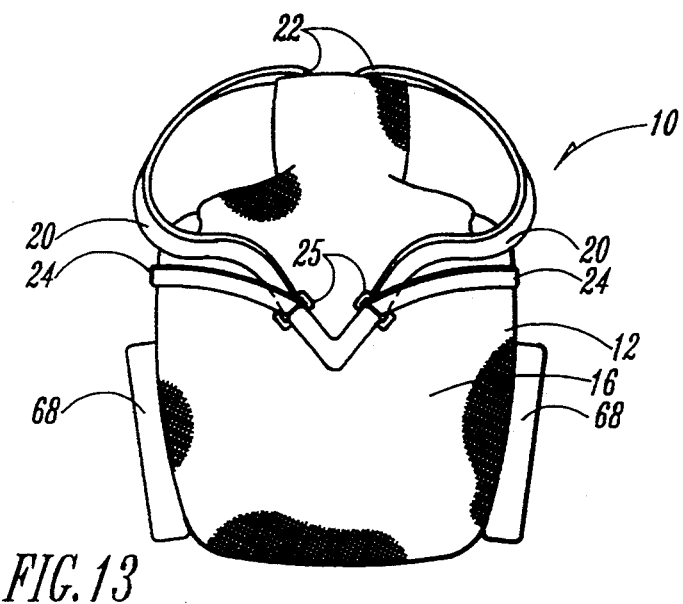
FIG. 13 is a rear elevation view showing a pair of auxiliary pads secured to the device.

Each side portion 14 of the jacket 12 also has a side pocket 56 for receiving a rigid or semi-rigid support plate 58, as seen in FIGS. 8 and 9. The plate 58 includes a vertical slot 60 therein to accommodate a vertical stitch 62 in the pocket 56. Plates 58 provide lateral trunk support for the patient. Each pocket 56 includes an access opening which can be closed with VELCRO or any other convenient closure means.

The front apron 18 includes a pocket 64 for receiving a front plate 66. Thus, a three point pressure system is defined by plate 66, thoracic band 38, and pelvic band 40. These three pressure points cooperate to provide proper support for the patient's spine. The pocket 64 has an access opening at the top which can be closed by any convenient means, such as VELCRO.

An auxiliary side support pad can be secured to each side portion 14 of the jacket 12 so as to provide additional lateral trunk support when the patient is sitting in a chair. Preferably, auxiliary pads 68 are secured to the side portions 14 by VELCRO. For example, the side portions 14 may include the loop portion 70 and the auxiliary pad includes the hook portion 72 of the cooperating VELCRO strips. Thus, the auxiliary pads 68 can be easily attached to and removed from the side portions 14 of the jacket 12. Each auxiliary pad 68 includes a layer of padding and a rigid or semi-rigid support plate 74. An access opening allows the padding and support plate to be removed when the fabric of the auxiliary pad needs to be cleaned. The access opening in the auxiliary pad can be closed in any convenient manner, such as VELCRO or a zipper.

The thoracic lumbar sacral orthosis device of the present invention is a customized restorative device providing corrective support to the upper and lower spine. The device limits motion in the lumbar and lower thoracic spine, and limits the rotation of the thoracic spine. The device also provides mild hyperextension or flexion of the lumbosacral joint. The device also controls slouching and stabilizes the trunk from undesired lateral deviation. The jacket 12 is made of a water repellant fabric which complies with health and safety standards, and provides good skin integrity, while being easy to clean and maintain.

The brace member 36 of the device 10 is molded for each patient. First, the length of the patient from under the axilla to the top of the greater trochanter is measured while the patient is standing, seated in a straight back chair, or laying face down on a bed. The brace member 36 is removed from the padding member 30. The brace member 36 is positioned on the patient's spine, with the bottom edge of the pelvic band placed approximately ½ inch above the greater trochanter or in line with the great SacroSciatic Notch. The paraspinal bars 42 are heated, for example with a heat gun, so as to contour to the patient's thoracic, lumbar-sacral spine so as to avoid migration. The upper extensions 44 of the paraspinal bars are also heated and molded to conform to the patient's upper thoracic region. The pelvic band is also heated and molded to conform to the patient's hips. The thoracic band 38 is heated and molded to conform to the patient's posterior thoracic area, with the terminal ends 46 fitting appropriately to the lateral chest wall of the patient. In molding the brace member 36, it is desirable to avoid pressure points. When molding of the brace member 36 is complete, the respective ends of the brace member are inserted in the pocket in the padding member 30 so that the brace member is mounted on the padding member. The support plate 66 in the front apron 18 may also be heated and molded to conform to the patient's upper abdomen. Side support plates 58 may also be heated and molded to conform to the patient's lateral chest.

When the brace member 36 and each of the support plates 58, 66 cool, they will maintain the molded shape due to the high memory properties of the material. If necessary, the brace member or plates may be reheated and remolded.

To place the device 10 on a patient, the padding member 30 and brace member 36 are positioned in the jacket compartment, and the support plates 58 and 66 are placed in their respective pockets. One side of the straps 27 for the front apron 18 are released such that the patient can slip his or her arms through the axilla straps 20 and the jacket can be positioned around the torso. The ends of the straps for the front apron are then secured through loops 28 and secured such that the apron is snug, but preferably not tightly fitted. The axilla straps 20 are also adjusted for a snug fit. The front apron straps can be loosened to reduce abdominal pressure when the patient is sitting. When the patient is sitting, auxiliary pads 68 may also be attached to the jacket 12 to provide additional support.

The invention has been shown and described above in connection with the preferred embodiment, and it is understood that many modifications, substitutions and additions may be made which are within the intended broad scope of the invention. From the foregoing, it can be seen that the present invention accomplishes at least all of the stated objectives.

What is claimed is:

1. A thoracic lumbar sacral orthosis device comprising:
   a jacket having opposite side portions, a back portion, the back portion being integrally formed with the side portions, a compartment formed within the side portions and back portions;
   padding means removably fit within the compartment;
   brace means removably positioned within compartment such that the padding means is between the brace means and a person's torso when the jacket is worn; and
   a pair of adjustable straps secured to the jacket and adapted to extend over the person's shoulders and under the arms so as to prevent slumping.

2. The device of claim 1 wherein the brace means includes a pelvic band, a thoracic band, and paraspinal bars extending between the pelvic band and thoracic band.

3. The device of claim 2 wherein the paraspinal bars are elongated and have a S-shaped curve to maintain the natural curve of the person's spine.

4. The device of claim 1 wherein the brace means is constructed of a moldable, flexible material having high memory properties.

5. The device of claim 1 wherein the jacket has a closable opening for access to the compartment.

6. The device of claim 1 further comprising a pair of side support pads removably secured to respective side portions of the jacket.

7. A thoracic lumbar sacral orthosis device comprising:
   a jacket having opposite side portions, a back portion, the back portion being integrally formed with the side portions, a compartment formed within the side portions and back portions;
   padding means removably fit within the compartment;
   brace means removably positioned within the compartment such that the padding means is between the brace means and a person's torso when the jacket is worn; and
   each side portion including a pocket with removable support means therein for providing lateral trunk stability.

8. A thoracic lumbar sacral orthosis device comprising:
   a jacket having opposite side portions, a back portion, the back portion being integrally formed with the side portions, a compartment formed within the side portions and back portions;
   padding means removably fit within the compartment;
   brace means removably positioned within the compartment such that the padding means is between the brace means and a person's torso when the jacket is worn; and
   the padding means including attachment means for releasably attaching the brace means thereto.

9. The device of claim 8 wherein the pelvic band and thoracic band each have opposite lateral ends, and the paraspinal bars each have opposite upper ends, the attachment means including a plurality of pockets on the padding means for removably receiving the respective ends of the pelvic and thoracic bands and paraspinal bars.

10. A spinal support brace comprising:
    a moldable brace means including vertically spaced apart bands adapted to extend across a person's back and having opposite lateral ends extending around the person's sides, and pair of horizontally spaced apart bars interconnecting the bands and adapted to extend along a person's back on each side of the spine;
    padding means removably secured to the brace means so as to reside between the person's torso and the brace means;
    pocket means on the padding means for removably receiving the ends of the bands so as to removably mount the brace means on the padding means; and
    securement means for securing the pad means and brace means to the person's torso, the securement means including a pair of straps extending over the person's shoulders and at least one strap extending across the person's abdomen.

11. A spinal support brace comprising:
    a moldable brace means including vertically spaced apart bands adapted to extend across a person's back and having opposite lateral ends extending around the person's sides, and pair of horizontally spaced apart bars interconnecting the bands and adapted to extend along a person's back on each side of the spine;
    padding means removably secured to the brace means so as to reside between the person's torso and the brace means;
    pocket means on the padding means for removably receiving the ends of the bands so as to removably mount the brace means on the padding means;
    securement means for securing the pad means and brace means to the person's torso; and
    soft enclosure means for enclosing the padding means and brace means, the securement means being adjustably attached to the enclosure means.

12. The brace of claim 11, wherein the enclosure is U-shaped, with a back portion, opposite side portions and an internal compartment therein for holding the brace means and padding means.

13. The brace of claim 12 wherein the side portions each have a pocket with a removable plate member therein for providing lateral trunk stability.

14. The brace of claim 12 further comprising a pair of pads removably fastening to respective side portions.

15. The brace of claim 12 further comprising a front apron releasably interconnecting the side portions and extending across the person's abdomen.

* * * * *